US00PP10094P

United States Patent [19]

Zaiger et al.

[11] Patent Number: Plant 10,094

[45] Date of Patent: Nov. 4, 1997

[54] PEACH TREE "SNOW KIST"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 697,574

[22] Filed: Aug. 27, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach tree which has the following unique combination of features that are outstanding in a new variety:

1. Heavy and regular bearer of fruit.
2. Production of large, firm, white flesh fruit.
3. Early maturity of fruit.
4. Large tree size with vigorous, upright growth.
5. Fruit with a high degree of attractive red skin color.
6. Fruit with very good flavor and eating quality.

1 Drawing Sheet

ORIGIN OF THE VARIETY

The present new variety of peach tree was developed by us in our experimental orchard located near Modesto, Calif., as a first generation cross between two selected seedlings with field identification numbers 36EB86 and 5GB8. The maternal parent (36EB86) originated from an open pollinated seedling selection that was selected from a cross between May Grand Nectarine (U.S. Plant Pat. No. 2,794) with a peach of unknown parentage. The pollen parent (5GE8) originated from a selected seedling from a cross between Fayette Peach (non-patented) with Royal April Peach (U.S. Plant Pat. No. 3,411) that was crossed with May Crest Peach (U.S. Plant Pat. No. 4,064). We grew and maintained a large group of these first generation seedlings under close observation, one such early maturing white flesh seedling, which is the present variety, exhibited the distinctive desirable fruit characteristics described above and was selected for asexual reproduction and commercialization.

ASEXUAL REPRODUCTION OF THE VARIETY

Asexual reproduction of the new and distinct peach tree was by budding, as performed by us in our experimental orchard located near Modesto, Calif., and shows that such reproductions run true to the original tree and all characteristics are established and transmitted through succeeding asexual propagations.

SUMMARY OF THE VARIETY

The present new and distinct variety of peach tree is of large size, vigorous, upright growth and a productive and regular bearer of large size, firm, white flesh, clingstone fruit with very good flavor and eating quality. The fruit is further characterized by holding firm 4 to 5 days after maturity (shipping ripe), being relatively uniform in ripening, having firm, white flesh with good handling and shipping quality. In comparison to the early maturing May Crest Peach (U.S. Plant Pat. No. 4,064), the new variety has greater production of fruit, has white instead of yellow flesh, has a more attractive red skin color, and matures in approximately the same maturity season.

BRIEF DESCRIPTION OF THE PHOTOGRAPH

The accompaning photographic illustration shows a reproduction in color of typical specimens of the foliage and fruit of our new and distinct variety of peach tree. The illustration shows the upper and lower surface of the leaves and the exterior and sectional view of a fruit divided in the suture plane to reveal flesh coloration, pit cavity and a stone remaining in place. The photograph was taken shortly after being picked at maturity (firm ripe) and the colors are as nearly true as is reasonably possible in a color representation of this type.

DESCRIPTION OF THE VARIETY

The following is a detailed botanical description of the present new peach tree, its flowers, foliage and fruit as based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Shape.*—Normally pruned to vase shape.
- *Bearer.*—Regular.
- *Production.*—Productive.

Trunk:
- *Size.*—Large.
- *Texture.*—Medium shaggy.
- *Color.*—Brown to soot brown (5-E-3) to (5-F-5).

Branches:
- *Size.*—Medium.
- *Texture.*—Smooth to medium rough, varies with age of growth.
- *Lenticels.*—Medium number. Large size.
- *Color.*—Light brown to brown (5-D-6) to (5-E-6).

Leaves:
- *Size.*—Medium to large. Average length 5½". Average width 1⅝".
- *Form.*—Lanceolate, pointed.
- *Margin.*—Crenate.
- *Texture.*—Smooth.
- *Thickness.*—Medium.
- *Petiole.*—Medium length. Medium thickness.
- *Glands.*—Number varies from 1 to 3. Average number 2. Reinform. Positioned on upper portion of petiole and lower portion of leaf blade.

*Color.*—Upper surface — green to dark green (28E-6) to (28-E-8). Lower surface — dull green to green (28-D-6) to (28-D-7).

Flower buds:

*Size.*—Medium to large.

*Form.*—Plump.

*Length.*—Medium.

*Pubescence.*—Pubescent.

Flowers:

*Size.*—Large, showy.

*Blooming period.*—Date of first bloom — Mar. 4, 1994. Date of full bloom — Mar. 10, 1994. Varies slightly with climatic conditions.

*Pollen.*—Present.

*Color.*—Pink.

Fruit:

*Maturity when described.*—Firm ripe.

*Date of first picking.*—May 17, 1994.

*Date of last picking.*—May 21, 1994.

*Size.*—Large, comparatively uniform. Average diameter axially 2½" to 2¾". Average transversely in suture plane 2½" to 2¾".

*Form.*—Nearly globose. Slightly flattened at stem end. Slight apical point.

*Suture.*—Shallow, nearly smooth, extends from base to apex.

*Ventral surface.*—Nearly rounded.

*Cavity.*—Rounded to slightly elongated in suture plane. Average depth 7/16". Average breadth ⅞".

*Base.*—Retuse.

*Apex.*—Usually slight pistil point, varies from round to slight point.

Flesh:

*Ripens.*—Evenly.

*Texture.*—Firm.

*Juice.*—Moderate.

*Fibers.*—Few, small, tender.

*Amygdalin.*—Undetected.

*Aroma.*—Moderate.

*Flavor.*—Very good.

*Eating quality.*—Very good.

*Color.*—White to yellowish white (2-A-1) to (2-A-2). Pit cavity — grayish white to pale gray (1-B-4) to (1-B-5).

Skin:

*Thickness.*—Medium.

*Texture.*—Medium.

*Tendency to crack.*—None.

*Down.*—Moderate. Medium length.

*Color.*—Ground color — white to pinkish white (9-A-1) to (9-A-2). Nearly overspread with light red to red blush (9-A-7) to (9-D-8), some areas with mottled red pattern.

Stone:

*Type.*—Clingstone.

*Size.*—Medium to large. Average length 1¼". Average breadth 1". Average thickness ⅝".

*Form.*—Usually obovate, varies from ovate to obovate.

*Base.*—Mostly straight, varies from straight to slightly rounded.

*Apex.*—Slightly pointed, varies from slightly pointed to nearly rounded.

*Sides.*—Equal to unequal.

*Tendency to split.*—Slight.

*Surface.*—Furrowed toward apex, pitted throughout, heavier toward base, pits vary from round to elongated.

*Color.*—Tan to light brown (7-C-4) to (7-D-5).

Use: Dessert. Market, local and long distance.

Keeping quality: Good.

Shipping quality: Good.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth and being a productive and regular bearer of large, white flesh clingstone fruit with very good flavor and eating quality; the fruit is further characterized by having firm white flesh with good handling and shipping quality, having an attractive red skin color and ripening in the early maturing season, approximately the same season as the early maturing yellow flesh May Crest Peach (U.S. Plant Pat. No. 4,064).

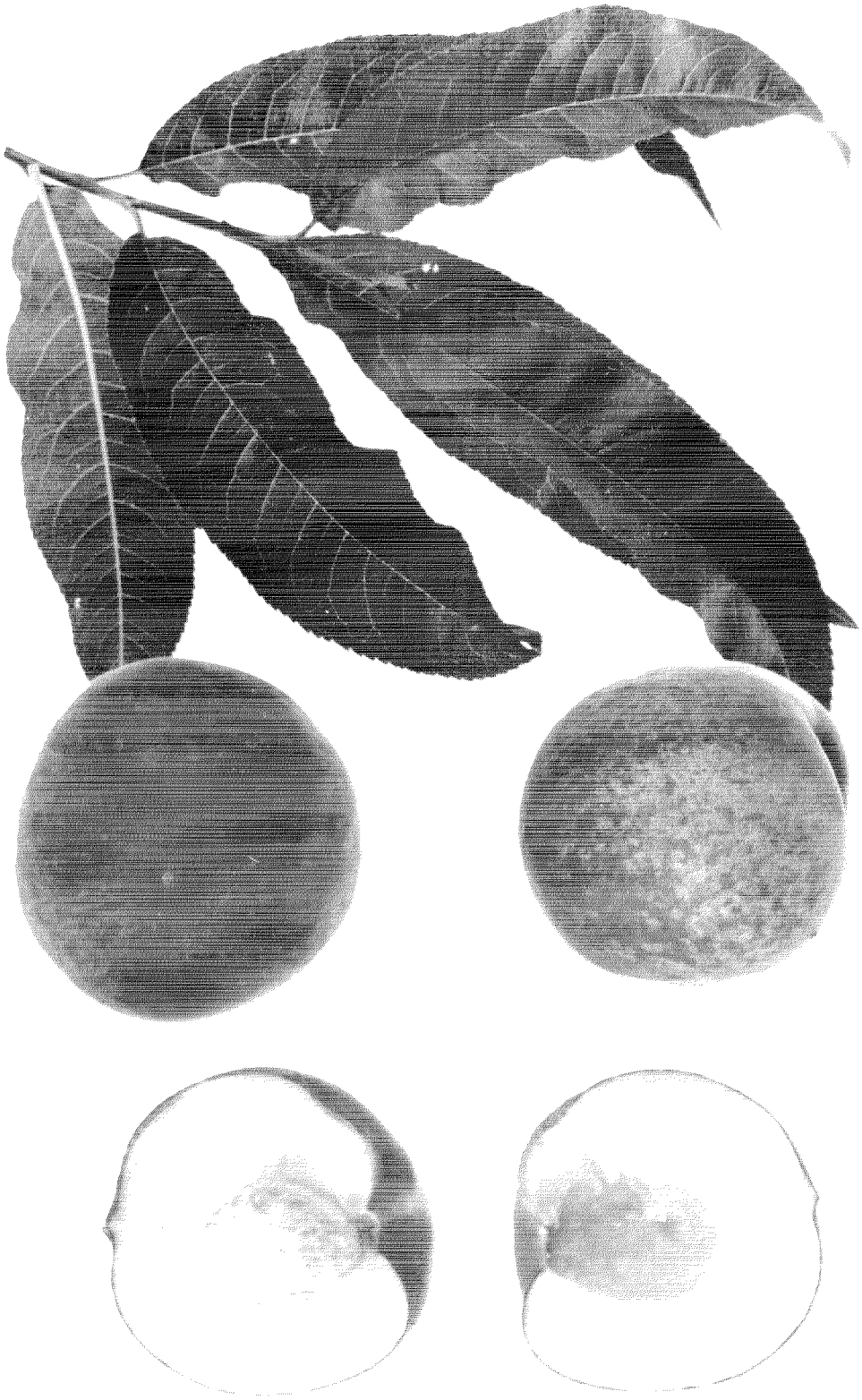

* * * * *